United States Patent
Anderson et al.

(10) Patent No.: US 7,278,431 B2
(45) Date of Patent: Oct. 9, 2007

(54) DEVICE FOR SMOOTHING KERATINOUS SURFACES

(75) Inventors: Paul M. Anderson, Lincroft, NJ (US); Lisa F. Baumgarten, New York, NY (US); Antonette Bivona, Bayside, NY (US); John D. Butcher, Scotch Plains, NJ (US); Ingrid Yung-I Chen, New York, NY (US); Emily M. Cohen, New York, NY (US); Jeffery F. Feng, St. Louis, MO (US); Stacey Leigh Grabiner, Westfield, NJ (US); Jayne H. Lynch, St. Louis, MO (US); Bryce G. Rutter, St. Louis, MO (US); Heather S. Sopczynski, New York, NY (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 11/073,912

(22) Filed: Mar. 7, 2005

(65) Prior Publication Data
US 2006/0196520 A1    Sep. 7, 2006

(51) Int. Cl.
*A45D 29/18* (2006.01)
(52) U.S. Cl. .................................... 132/76.4
(58) Field of Classification Search ............. 132/76.4, 132/75.6, 76.5; 15/171, DIG. 1, 167.1, 167; 451/540, 547; 4/606; 16/430; 606/131; D28/56, 57, 59
See application file for complete search history.

(56) References Cited

U.S. PATENT DOCUMENTS

| 338,245 | A | * | 3/1886 | Broadhurst | 132/76.4 |
|---|---|---|---|---|---|
| 1,643,164 | A | * | 9/1927 | MacDougall | 132/74.5 |
| 2,591,331 | A | | 4/1952 | Baumbach | 15/160 |
| 2,735,434 | A | * | 2/1956 | Rossett | 132/76.4 |
| 3,040,337 | A | | 6/1962 | Fjelstad | 4/184 |
| 3,131,701 | A | | 5/1964 | Emerson | 132/76.4 |
| 3,612,044 | A | | 10/1971 | Gurroin | 128/62 |
| 3,706,316 | A | * | 12/1972 | Konagai | 132/76.4 |
| 4,480,351 | A | * | 11/1984 | Koffler | 15/187 |
| D326,327 | S | | 5/1992 | Sue | D24/214 |
| 5,382,189 | A | | 1/1995 | Arendall | 451/557 |
| 5,781,958 | A | * | 7/1998 | Meessmann et al. | 15/167.1 |
| 5,784,722 | A | | 7/1998 | Uretz et al. | 2/244.1 |
| D409,336 | S | | 5/1999 | Stein | D28/63 |
| 5,913,313 | A | * | 6/1999 | Brunderman | 132/76.4 |
| 6,210,350 | B1 | * | 4/2001 | Finch | 601/136 |
| 6,226,811 | B1 | * | 5/2001 | Fagan | 4/606 |
| 6,253,407 | B1 | | 7/2001 | Bjelkevig | 15/160 |
| D476,446 | S | | 6/2003 | Chen | D28/59 |
| 6,708,351 | B2 | | 3/2004 | Sullinger | 4/559 |
| 2004/0254587 | A1 | * | 12/2004 | Park | 606/131 |

FOREIGN PATENT DOCUMENTS

WO    WO90/01280    *    2/1990

* cited by examiner

*Primary Examiner*—Todd E. Manahan
(74) *Attorney, Agent, or Firm*—Joy S. Goudie

(57) ABSTRACT

A skin grooming device comprising a planar surface for removable attachment to a stationary surface, having affixed thereto an undulating abrasive block for use in abrading rough, dead, or dry skin from keratinous surfaces and a method for grooming skin using the device.

8 Claims, 2 Drawing Sheets

DEVICE FOR SMOOTHING KERATINOUS SURFACES

TECHNICAL FIELD

The invention is in the field of devices for smoothing and abrading rough, dead, or dry skin on keratinous surfaces such as feet, elbows, knees and the like.

BACKGROUND OF THE INVENTION

There are a variety of devices for removing rough skin from the soles of the feet or similar keratinous surfaces. For example, U.S. Design Patent No. 476,446 depicts a handled tool having a head to which an abrasive surface is affixed. The user grips the handle with the fingers and uses the abrasive surface to remove dead skin and otherwise smooth the skin on the desired surface. One problem with this type of device is that it is difficult for elderly or disabled users to handle. They must be able to grip the handle and reach far enough toward the sole of the foot in order to contact the abrasive surface with the sole of the foot. For those that have limited dexterity, this can be a cumbersome operation.

U.S. Pat. No. 2,591,331 depicts a foot brush used for cleaning feet in the shower or bath tub. The user inserts the foot in a "box", which contains bristles along the bottom and sides, and moves the foot backward and forward across the bristle tips to remove dirt and grime from the foot. While this device may be good for cleaning feet, the bristles are not typically sufficient for abrading dead or rough skin from the soles of the feet.

U.S. Pat. No. 6,780,351 depicts a device for removing calluses and dry skin from the soles of the feet. The device has a concave abrasive surface attached to a pedestal having suction cups on the bottom surface thereof for attachment to the shower or tub floor. The suction cups adhere the device to the floor, permitting the user to rub the sole of the foot on the abrasive surface to remove dead or rough skin. While this type of device is very convenient and addresses issues found with handled devices, the abrasive circular concave abrasive surface is not the optimum configuration for abrading dead or rough skin on the entire sole of the foot.

There is a need for a pedicure device for smoothing and abrading skin on the soles of the feet and other keratinous surfaces, which works for users that have limited dexterity.

It is an object of the invention to provide a pedicure device for smoothing and abrading skin on the soles of the feet or other keratinous surfaces such as elbows or knees, that can be affixed to a stationary surface such as the floor, permitting the user to treat the desired surface by simply rubbing it on an abrasive surface without having to bend over or engage in other bodily contortions.

It is also an object of the invention to provide a pedicure device for smoothing and abrading skin on the soles of the feet that has an undulating abrasive surface that facilitates grooming on all areas of the soles of the feet.

It is also an object of the invention to provide a pedicure device for smoothing and abrading skin on the soles of the feet, elbows, knees, or the like, that can be removably affixed to a floor or wall surface while in use, and removed from that surface if desired.

It is a further object of the invention to provide a pedicure device for smoothing and abrading skin on the soles of the feet that does not involve use of the hands.

DETAILED DESCRIPTION OF THE DRAWINGS

Figure 1:
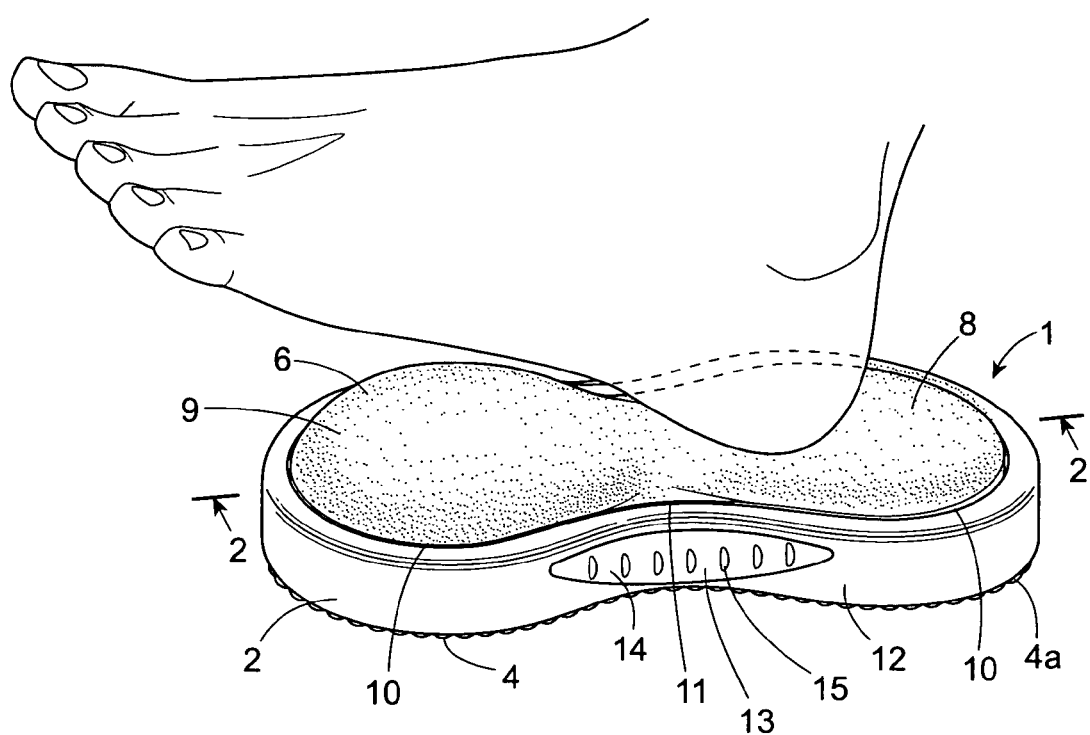
FIG. 1: is a perspective view of a user using the device of the invention, in particular the concave portion, to treat the soles of the feet.
Figure 4:
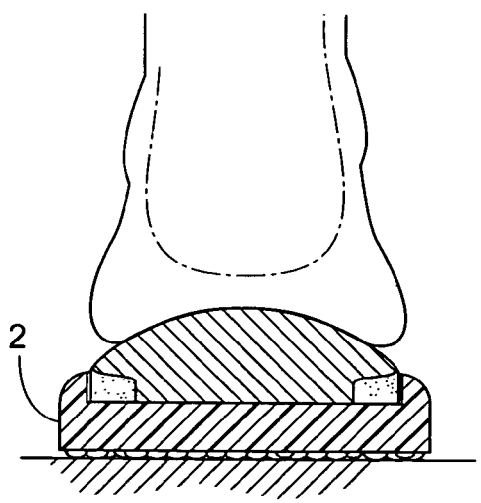
FIG. 4: is a cross-sectional view taken across 4-4 of FIG. 3 showing a user using the convex portion of the abrasive surface to treat the sole of the foot.
Figure 5:
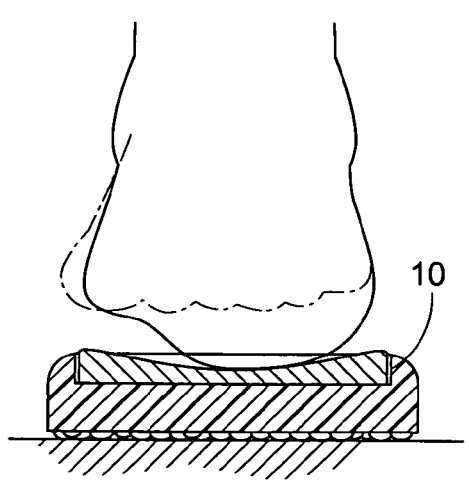
FIG. 5: is a cross sectional view taken across 5-5 of FIG. 2 showing a user using the concave portion of the abrasive surface to treat the sole of the foot.
Figure 2:
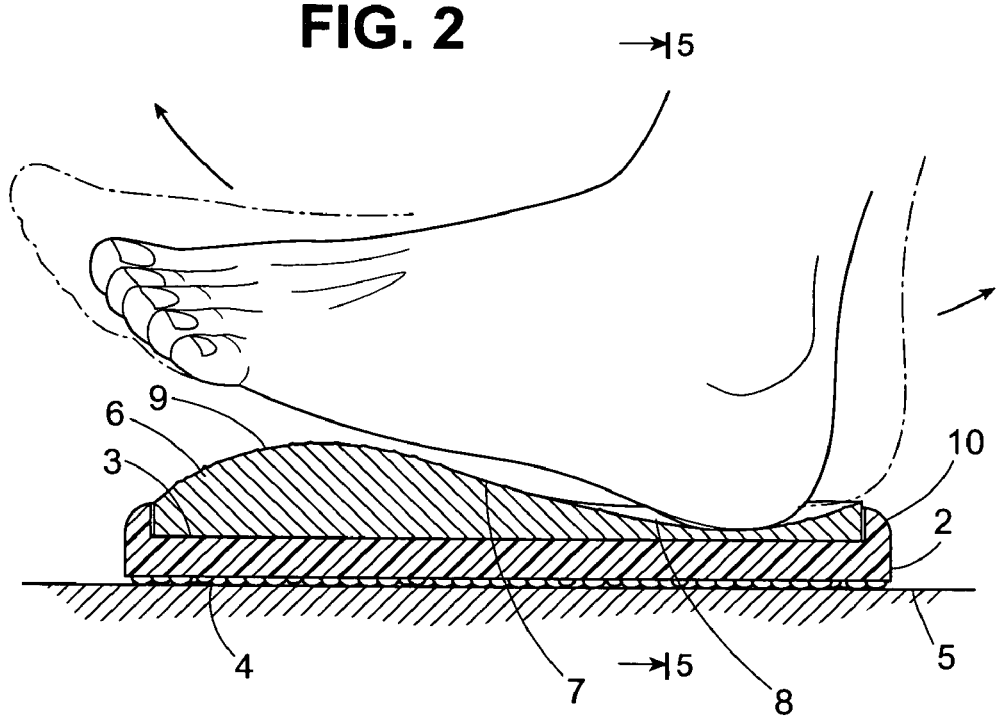
FIG. 2: is a cross-sectional view taken across 2-2 of FIG. 1, showing a user using the concave portion of the device of the invention to treat the soles of the feet.
Figure 3:
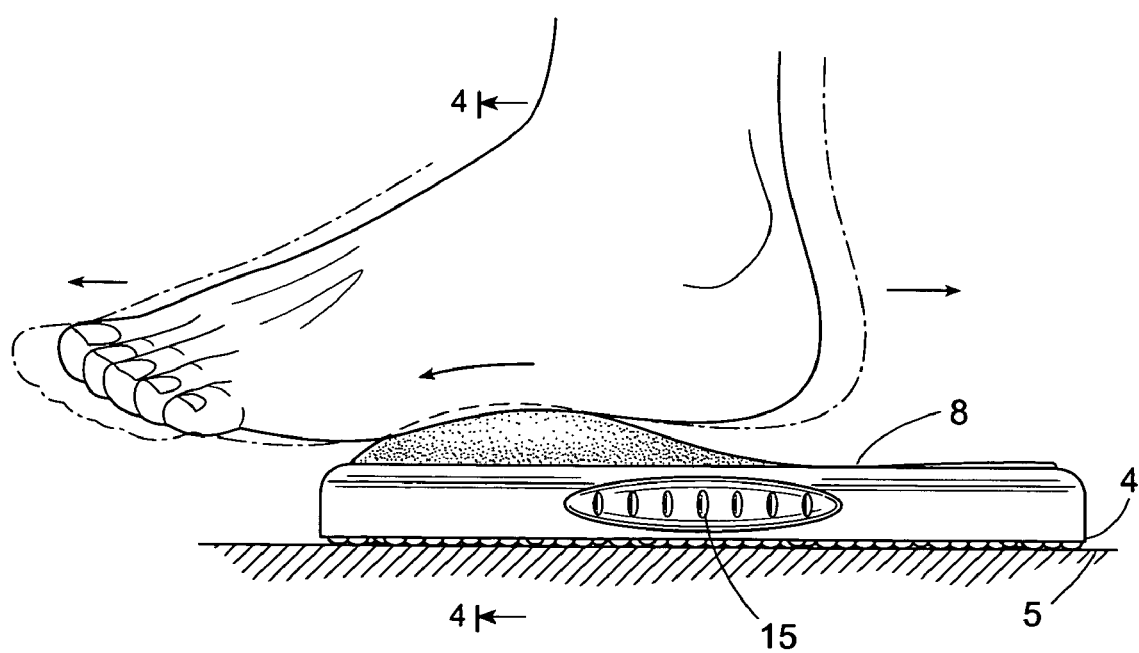
FIG. 3: further shows a user using the device of the invention to treat the soles of the feet by using the convex surface to treat the middle section of the foot.

The invention is directed to a device 1 for treating the soles of the feet or possibly other body surfaces such as elbows, knees, or the like, or similar keratinous surfaces, to remove rough, dead, dry skin, or otherwise smooth the skin. The device 1 has a planar surface 2 that forms the bottom portion of the device. The planar surface 2 has a top surface 3 and a bottom surface 4. To the bottom surface 4 is attached a web 4A or something similar that enables the bottom surface 4 of planar surface 2 to be removably affixed to a stationary surface 5 such as the floor of a tub or the wall of a shower. Web 4A may be in the form of a flexible thermoplastic mesh that has adhesive properties sufficient to enable web 4A to cause planar surface 2 to be removably affixed to the desired stationary surface 5 while device 1 is being used to treat the soles of the feet. Alternatively web 4A may consist of suction cups. Typically web 4A will be made of a thermoplastic mesh with sufficient adhesivity such that the bottom surface 4 of planar surface 2 to which it is attached will cause the device 1 to be affixed to stationary surface 5 with sufficient strength to enable device 1 to be used for its intended purpose without becoming dislodged, yet not affixed so securely that device 1 cannot be readily dislodged from stationary surface 5 when desired.

On the top surface 3 of bottom planar surface 2 an abrasive block 6 is affixed. Abrasive block 6 has an undulating top surface 7 comprised of at least one concave portion 8 and at least one convex portion 9. Abrasive block 6 is made of abrasive stone such as pumice or the like, with a grain, or degree of abrasivity sufficient to enable abrading rough, dry, or dead skin from the soles of the feet or other keratinous surfaces, when the sole of the foot is rubbed across the abrasive block 6. Abrasive block 6 may be secured onto the top surface 3 by glue or similar adhesive means such that abrasive block 6 is non-removably secured to top surface 3.

Preferably bottom planar surface 2 has an indentation 10 forming a recess into which abrasive block 6 can be fitted and secured. Preferably both bottom planar surface 2 and abrasive block 6 have an external circumference that is in what is referred to as a "bean" or generally figure 8 shape with the concave portion 8 forming one side of the bean or eight and convex portion 9 the other side. Preferably concave portion 8 and convex portion 9 are widened circular portions 10 with the center section between concave portion 8 and convex portion 9 having a slightly reduced width 11.

Bottom planar surface 2 has side edges 12. In the mid portion 13 of side edges 12 there may be affixed a thermoplastic gripping member 14 in the event the user desires to hold device 1 in the hands. Gripping member 14 will facilitate the grip. In addition, gripping member 14 will facilitate user's ability to both affix and remove device 1 from stationary surface 5 when desired. Thermoplastic gripping member 14 may have cuts 15 in the sides to further provide a surface that facilitates grip.

The device 1 of the invention facilitates grooming of the feet in a manner that does not involve use of the hands if not desired. The device 1 may also be gripped in the hands if desired by the consumer, and used to treat other areas of the skin such as elbows, knees, and so on.

The invention is also directed to a method for abrading or removing rough, dead, or dry skin from keratinous surfaces such as the soles of the feet, elbows, or knees by treating the skin with the device of the invention.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A skin grooming device comprising a bottom planar surface for removable attachment to a stationary surface, and a top planar surface having an indentation forming a recess into which is affixed an undulating abrasive block having a concave portion and a convex portion and having an external circumference in a figure 8 shape with one side of the figure 8 forming the concave portion and one side of the figure 8 forming the convex portion with both portions being substantially identical in circumference for use in abrading rough, dead, or dry skin from keratinous surfaces.

2. The device of claim 1 wherein the concave and convex portions having a substantially identical circumference are separated by a mid section having a width that is less than the figure 8 portions.

3. The device of claim 1 wherein the abrasive block is made of pumice.

4. The device of claim 1 wherein said bottom planar surface having side edges has at least one hand gripping member affixed to at least one side edge.

5. The device of claim 4 wherein the gripping member is a flexible thermoplastic material with adhesive properties.

6. The device of claim 5 wherein the flexible thermoplastic material has slits in the side.

7. The device of claim 1 wherein the abrasive block is glued into the indentation of the planar surface.

8. A device for removing skin from the bottoms of the feet during a shower or bath, said device comprised of a bottom planar surface having an adhesive web for removable attachment to the shower or tub surface, and a top planar surface having an indentation forming a recess into which is permanently affixed an undulating pumice block in the form of a figure 8 having a concave portion and a convex portion and having an external circumference in a figure 8 shape with one side of the figure 8 forming the concave portion and one side of the figure 8 forming the convex portion with both portions being substantially identical in circumference, wherein said bottom planar surface has side walls having hand gripping members affixed thereto.

* * * * *